(12) United States Patent
Alrakah

(10) Patent No.: US 12,018,911 B2
(45) Date of Patent: Jun. 25, 2024

(54) MANAGING OPERATION OF A WEAPON

(71) Applicant: Saudi Arabian Oil Company, Dhahran (SA)

(72) Inventor: Badr Mahdi Alrakah, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 286 days.

(21) Appl. No.: 17/500,692

(22) Filed: Oct. 13, 2021

(65) Prior Publication Data

US 2023/0114957 A1    Apr. 13, 2023

(51) Int. Cl.
| F41C 33/02 | (2006.01) |
| A61B 5/00 | (2006.01) |
| G06F 21/32 | (2013.01) |
| F41A 17/06 | (2006.01) |

(52) U.S. Cl.
CPC .......... *F41C 33/029* (2013.01); *A61B 5/0022* (2013.01); *G06F 21/32* (2013.01); *F41A 17/063* (2013.01); *F41A 17/066* (2013.01)

(58) Field of Classification Search
CPC ........ F41C 33/00; F41C 33/02; F41C 33/029; F41C 33/0209; F41C 33/0236; F41C 33/0245
See application file for complete search history.

(56) References Cited

U.S. PATENT DOCUMENTS

| 9,752,840 | B1 | 9/2017 | Betro |
| 9,958,228 | B2 | 5/2018 | Stewart et al. |
| 10,359,249 | B2 | 7/2019 | Stewart et al. |
| 10,365,057 | B2 | 7/2019 | Black et al. |
| 10,866,054 | B2 | 12/2020 | Stewart et al. |
| 2010/0315235 | A1 | 12/2010 | Adegoke et al. |
| 2016/0165192 | A1 | 6/2016 | Saatchi et al. |
| 2016/0286156 | A1* | 9/2016 | Kovac ............... G06Q 50/26 |

(Continued)

FOREIGN PATENT DOCUMENTS

| WO | WO 2017048313 | 3/2017 |
| WO | WO 2017204792 | 11/2017 |

OTHER PUBLICATIONS

Bodyworn.com [online], "Smart holster sensor," 2020, retrieved Oct. 12, 2021 from URL<https://www.bodyworn.com/smart-holster-sensor>, 3 pages.

(Continued)

*Primary Examiner* — Benyam Haile
(74) *Attorney, Agent, or Firm* — Fish & Richardson P.C.

(57) ABSTRACT

A weapon assembly includes a weapon; a weapon holster configured to receive and support at least a portion of the weapon; and a controller that includes a biometric sensor and a weapon activation sensor. The controller perform operations including transmitting a signal generated by the weapon activation sensor that is indicative of at least one of a release of the portion of the weapon from the weapon holster or a discharge of the weapon; and transmitting a signal generated by the biometric sensor indicative of a biometric state of a user of the weapon subsequent to the release of the portion of the weapon from the weapon holster or the discharge of the weapon. The signal generated by the biometric sensor is processable by a control system to generate a biometric feedback to determine a predictive diagnosis for the user.

33 Claims, 9 Drawing Sheets

(56) References Cited

U.S. PATENT DOCUMENTS

| | | |
|---|---|---|
| 2017/0222676 A1 | 8/2017 | Piccioni |
| 2017/0241727 A1 | 8/2017 | Stewart et al. |
| 2017/0241728 A1 | 8/2017 | Stewart et al. |
| 2019/0063864 A1 | 2/2019 | Stewart et al. |
| 2020/0042797 A1* | 2/2020 | Lee .................. G06F 18/22 |
| 2022/0214127 A1* | 7/2022 | French .............. F41A 19/59 |

OTHER PUBLICATIONS

Digitaltrends.com [online], "New holster sensor detects when a cop's weapon is drawn, turns on nearby body cams," Feb. 28, 2017, retrieved Feb. 26, 2021 from URL<https://www.digitaltrends.com/cool-tech/axon-wireless-sensor-gun-camera/>, 8 pages.

Motorolasolutions.com [online], "Holster aware: Capture the events that matter," 2020, retrieved Oct. 12, 2021 from URL<https://www.motorolasolutions.com/content/dam/msi/docs/EA_Collaterals/ENGLISH/bwc/holster-aware-brochure.pdf>, 5 pages.

Prnewswire.com [online], "Gun drawn, camera on: New axon signal sidearm alerts body cams from holster," Feb. 27, 2017, retrieved Feb. 26, 2021 from URL<https://www.prnewswire.com/news-releases/gun-drawn-camera-on-new-axon-signal-sidearm-alerts-body-cams-from-holster-300413641.html>, 5 pages.

* cited by examiner

320 ⬎

322 — Activating a weapon assembly that includes a weapon and a weapon holster that includes a controller.

324 — Generating a signal by a weapon activation sensor of the controller that is indicative of at least one of a release of the portion of the weapon from the weapon holster or a discharge of the weapon.

326 — Generating a signal by a biometric sensor of the controller that is indicative of a biometric state of a user of the weapon.

328 — Generating a signal by a GPS sensor of the controller that is indicative of a location of the user of the weapons.

330 — Receiving an alert associated with at least one of a biometric feedback in response to the generated signal by the biometric sensor or the location of the user.

```
WASP                                                — ☐ ✕
File  Edit  View  Window  Help
Map  | Alerts | Daily Report |                      Sign Out
```

Daily Report

Danger! currentTime Indicates a dangerous or potentially negative action.

Success! Indicates a successful or positive action.

Info! Indicates a neutral informative change or action.

Success! Indicates a successful or positive action.

Warning! Indicates a warning that might need attention.

Success! Indicates a successful or positive action.

FIG. 4C

MANAGING OPERATION OF A WEAPON

TECHNICAL FIELD

The present disclosure describes apparatus, systems, and methods for managing operation of a weapon.

BACKGROUND

Law enforcement and security personnel are often tasked with carrying and, at times, discharging a weapon, such as a handgun or other firearm, during the course of their duties. A location, time, and circumstances of such discharge can be critical information to the personnel as well as others, especially in managing an aftermath of the discharge.

SUMMARY

In an example implementation, a weapon management system includes a weapon assembly that includes a weapon and a weapon holster. The weapon holster is configured to receive and support at least a portion of the weapon and includes a controller that includes at least one biometric sensor and at least one weapon activation sensor. The system includes a control system that includes at least one interface configured to communicably couple to the controller and perform operations including identifying a signal generated by the at least one weapon activation sensor that is indicative of at least one of a release of the portion of the weapon from the weapon holster or a discharge of the weapon; identifying a signal generated by the at least one biometric sensor indicative of a biometric state of a user of the weapon subsequent to the at least one of the release of the portion of the weapon from the weapon holster or the discharge of the weapon; generating a biometric feedback in response to the identified signal generated by the at least one biometric sensor; and determining a predictive diagnosis for the user based at least in part on the generated biometric feedback.

In an aspect combinable with the example implementation, the controller further includes a GPS sensor, and the control system is configured to perform operation further including tracking a location of at the weapon holster, based on one or more signals from the GPS sensor, subsequent to identifying the signal generated by the at least one weapon activation sensor that is indicative of the at least one of the release of the portion of the weapon from the weapon holster or the discharge of the weapon.

In another aspect combinable with any of the previous aspects, the control system is configured to perform operations further including determining that the signal generated by the at least one weapon activation sensor is indicative of the discharge of the weapon; and determining a type of the discharge of the weapon.

In another aspect combinable with any of the previous aspects, the type of discharge of the weapon includes a misfire or a combat shot.

In another aspect combinable with any of the previous aspects, the operation of determining the type of the discharge of the weapon includes determining a time duration subsequent to the release of the portion of the weapon from the weapon holster; comparing the determined time duration against a pre-determined threshold time duration; and determining the type of the discharge of the weapon based on the comparison.

In another aspect combinable with any of the previous aspects, the operation of generating the biometric feedback in response to the identified signal generated by the at least one biometric sensor includes determining a level of biometric stress of the user based on the identified signal generated by the at least one biometric sensor; and storing the level of biometric stress in at least one database of the control system.

In another aspect combinable with any of the previous aspects, the level of biometric stress includes one of a low stress level, a medium stress level, or a high stress level.

In another aspect combinable with any of the previous aspects, the operation of determining the level of biometric stress of the user based on the identified signal generated by the at least one biometric sensor includes measuring at least one of a heart rate of the user, a galvanic skin response of the user, or a tension level of the user by the at least one biometric sensor.

In another aspect combinable with any of the previous aspects, the control system is configured to perform operations further including storing the determined predictive diagnosis for the user; and tracking a change in the determined predicative diagnosis for the user over time.

In another aspect combinable with any of the previous aspects, the control system is configured to perform operations further including generating an alert based at least in part on the generated biometric feedback; and transmitting the generated alert to a command center associated with the user.

In another aspect combinable with any of the previous aspects, the weapon includes a handgun.

In another example implementation, a computer-implemented method for managing a weapon includes identifying, with one or more hardware processors, an activation of a weapon assembly that includes a weapon and a weapon holster, the activation based on a signal from a controller of the weapon holster that includes at least one biometric sensor and at least one weapon activation sensor; identifying, with the one or more hardware processors, a signal generated by the at least one weapon activation sensor that is indicative of at least one of a release of the portion of the weapon from the weapon holster or a discharge of the weapon; identifying, with the one or more hardware processors, a signal generated by the at least one biometric sensor indicative of a biometric state of a user of the weapon subsequent to the at least one of the release of the portion of the weapon from the weapon holster or the discharge of the weapon; generating, with the one or more hardware processors, a biometric feedback in response to the identified signal generated by the at least one biometric sensor; and determining, with the one or more hardware processors, a predictive diagnosis for the user based at least in part on the generated biometric feedback.

In an aspect combinable with the example implementation, the controller further includes a GPS sensor.

Another aspect combinable with any of the previous aspects further includes tracking, with the one or more hardware processors, a location of at the weapon holster, based on one or more signals from the GPS sensor, subsequent to identifying the signal generated by the at least one weapon activation sensor that is indicative of the at least one of the release of the portion of the weapon from the weapon holster or the discharge of the weapon.

Another aspect combinable with any of the previous aspects further includes determining, with the one or more hardware processors, that the signal generated by the at least one weapon activation sensor is indicative of the discharge of the weapon; and determining, with the one or more hardware processors, a type of the discharge of the weapon.

In another aspect combinable with any of the previous aspects, the type of discharge of the weapon includes a misfire or a combat shot.

In another aspect combinable with any of the previous aspects, determining the type of the discharge of the weapon includes determining, with the one or more hardware processors, a time duration subsequent to the release of the portion of the weapon from the weapon holster; comparing, with the one or more hardware processors, the determined time duration against a pre-determined threshold time duration; and determining, with the one or more hardware processors, the type of the discharge of the weapon based on the comparison.

In another aspect combinable with any of the previous aspects, generating the biometric feedback in response to the identified signal generated by the at least one biometric sensor includes determining, with the one or more hardware processors, a level of biometric stress of the user based on the identified signal generated by the at least one biometric sensor; and storing, with the one or more hardware processors, the level of biometric stress in at least one database of the control system.

In another aspect combinable with any of the previous aspects, the level of biometric stress includes one of a low stress level, a medium stress level, or a high stress level.

In another aspect combinable with any of the previous aspects, determining the level of biometric stress of the user based on the identified signal generated by the at least one biometric sensor includes identifying, with the one or more hardware processors, one or more measurements of at least one of a heart rate of the user, a galvanic skin response of the user, or a tension level of the user by the at least one biometric sensor.

Another aspect combinable with any of the previous aspects further includes storing, with the one or more hardware processors, the determined predictive diagnosis for the user; and tracking, with the one or more hardware processors, a change in the determined predicative diagnosis for the user over time.

Another aspect combinable with any of the previous aspects further includes generating, with the one or more hardware processors, an alert based at least in part on the generated biometric feedback; and transmitting, with the one or more hardware processors, the generated alert to a command center associated with the user.

In another aspect combinable with any of the previous aspects, the weapon includes a handgun.

In another example implementation, an apparatus includes a tangible, non-transitory computer readable media that includes instructions that, when executed by one or more hardware processors, cause the one or more hardware processors to perform operations including identifying an activation of a weapon assembly that includes a weapon and a weapon holster, the activation based on a signal from a controller of the weapon holster that includes at least one biometric sensor and at least one weapon activation sensor; identifying a signal generated by the at least one weapon activation sensor that is indicative of at least one of a release of the portion of the weapon from the weapon holster or a discharge of the weapon; identifying a signal generated by the at least one biometric sensor indicative of a biometric state of a user of the weapon subsequent to the at least one of the release of the portion of the weapon from the weapon holster or the discharge of the weapon; generating a biometric feedback in response to the identified signal generated by the at least one biometric sensor; and determining a predictive diagnosis for the user based at least in part on the generated biometric feedback.

In an aspect combinable with the example implementation, the controller further includes a GPS sensor.

In another aspect combinable with any of the previous aspects, the operations further include tracking a location of at the weapon holster, based on one or more signals from the GPS sensor, subsequent to identifying the signal generated by the at least one weapon activation sensor that is indicative of the at least one of the release of the portion of the weapon from the weapon holster or the discharge of the weapon.

In another aspect combinable with any of the previous aspects, the operations further include determining that the signal generated by the at least one weapon activation sensor is indicative of the discharge of the weapon; and determining a type of the discharge of the weapon.

In another aspect combinable with any of the previous aspects, the type of discharge of the weapon includes a misfire or a combat shot.

In another aspect combinable with any of the previous aspects, the operation of determining the type of the discharge of the weapon includes determining a time duration subsequent to the release of the portion of the weapon from the weapon holster; comparing the determined time duration against a pre-determined threshold time duration; and determining the type of the discharge of the weapon based on the comparison.

In another aspect combinable with any of the previous aspects, the operation of generating the biometric feedback in response to the identified signal generated by the at least one biometric sensor includes determining a level of biometric stress of the user based on the identified signal generated by the at least one biometric sensor; and storing the level of biometric stress in at least one database of the control system.

In another aspect combinable with any of the previous aspects, the level of biometric stress includes one of a low stress level, a medium stress level, or a high stress level.

In another aspect combinable with any of the previous aspects, the operation of determining the level of biometric stress of the user based on the identified signal generated by the at least one biometric sensor includes identifying one or more measurements of at least one of a heart rate of the user, a galvanic skin response of the user, or a tension level of the user by the at least one biometric sensor.

In another aspect combinable with any of the previous aspects, the operations further include storing the determined predictive diagnosis for the user; and tracking a change in the determined predicative diagnosis for the user over time.

In another aspect combinable with any of the previous aspects, the operations further include generating an alert based at least in part on the generated biometric feedback; and transmitting the generated alert to a command center associated with the user.

In another aspect combinable with any of the previous aspects, the weapon includes a handgun.

In another example implementation, a weapon assembly includes a weapon; a weapon holster configured to receive and support at least a portion of the weapon; and a controller that includes at least one biometric sensor, at least one weapon activation sensor, and at least one interface configured to communicably couple to a control system, the controller configured to perform operations including transmitting, to the control system, a signal generated by the at least one weapon activation sensor that is indicative of at least one of a release of the portion of the weapon from the weapon holster or a discharge of the weapon; and transmitting, to the control system, a signal generated by the at least one biometric sensor indicative of a biometric state of a user of the weapon subsequent to the at least one of the release of the portion of the weapon from the weapon holster or the discharge of the weapon. The signal generated by the at least one biometric sensor is processable by the control system to generate a biometric feedback to determine a predictive diagnosis for the user.

An aspect combinable with the example implementation further includes a GPS sensor.

In another aspect combinable with any of the previous aspects, the controller is configured to perform operation further including transmitting, to the control system, a location of the user or the weapon holster based on one or more signals from the GPS sensor, subsequent to transmitting the signal generated by the at least one weapon activation sensor that is indicative of the at least one of the release of the portion of the weapon from the weapon holster or the discharge of the weapon; and receiving, from the control system, an alert associated with at least one of the generated biometric feedback or the location of the user of weapon holster.

In another aspect combinable with any of the previous aspects, the identified signal generated by the at least one biometric sensor is processable by the control system to determine a level of biometric stress of the user based on the identified signal generated by the at least one biometric sensor.

In another aspect combinable with any of the previous aspects, the level of biometric stress includes one of a low stress level, a medium stress level, or a high stress level.

In another aspect combinable with any of the previous aspects, the at least one biometric sensor includes at least one of a heart rate sensor, a galvanic skin response sensor, or a tension level sensor.

In another aspect combinable with any of the previous aspects, the weapon includes a handgun.

Implementations of a weapon alert safety protection system according to the present disclosure may include one or more of the following features. For example, a weapon alert safety protection system according to the present disclosure can help prevent stress and anxiety for remote security workforce and post recovery to reduce the risk of post-traumatic stress disorder (PTSD) among security and law enforcement personnel. As another example, a weapon alert safety protection system according to the present disclosure can improve operational efficiency in security situations and deployment.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIGS. 3A-3C are flowcharts that illustrate example methods performed with or by a weapon alert safety protection system according to the present disclosure.

FIGS. 4A-4C are illustrations of example graphical user interface (GUI) screens that are implemented by a weapon alert safety protection system according to the present disclosure.

DETAILED DESCRIPTION

Figure 1:
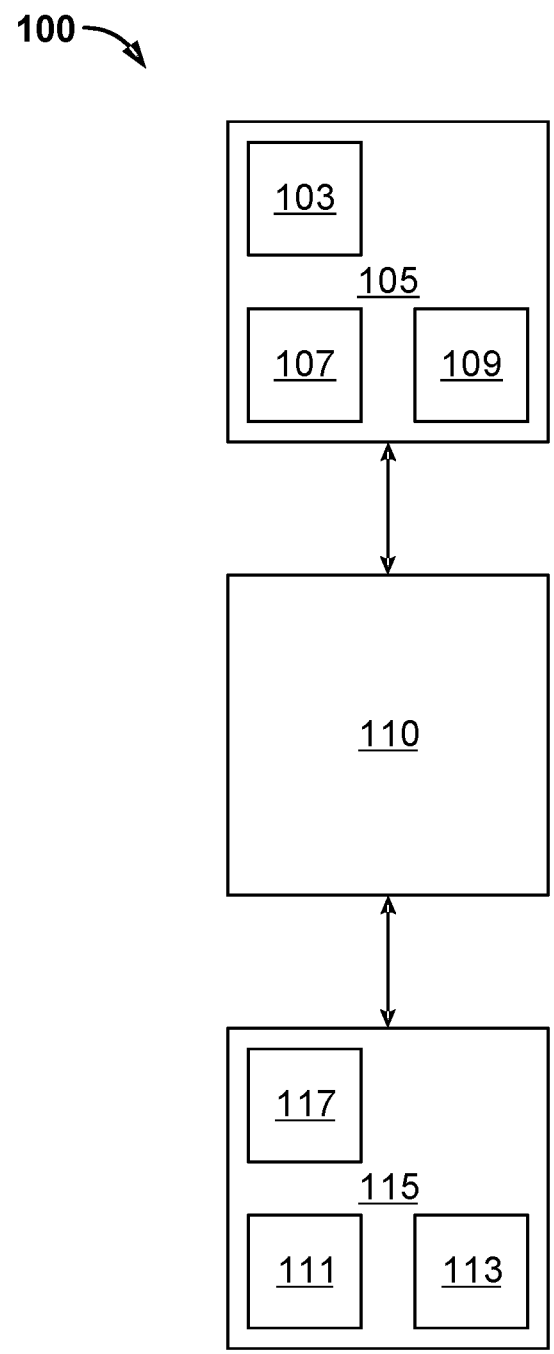
FIG. 1 is a schematic illustration of an example implementation of a weapon alert safety protection system according to the present disclosure.

FIG. 1 is a schematic illustration of an example implementation of a weapon alert safety protection system 100 according to the present disclosure. Generally, the weapon alert safety protection system 100 is includes in this example implementation include weapon hardware, a network system, and application and biofeedback loops that provide alerts and information in response to use of the weapon hardware. In this example of FIG. 1, the weapon alert safety protection system 100 includes a weapon assembly 115, a network 110, and a control system 105. As shown, each of the weapon assembly 115 and the control system 105 is enabled for bi-directional communication through the network 110, which can be wired, wireless, or a combination thereof, such that data and measurements gathered or generated by the weapon assembly 115 can be provided to the control system 105 through the network 110, while feedback, alerts, and other generated or calculated data (for example, based on the gathered data and measurements) can be provided from the control system 105 to the weapon assembly 115.

Figure 2A:
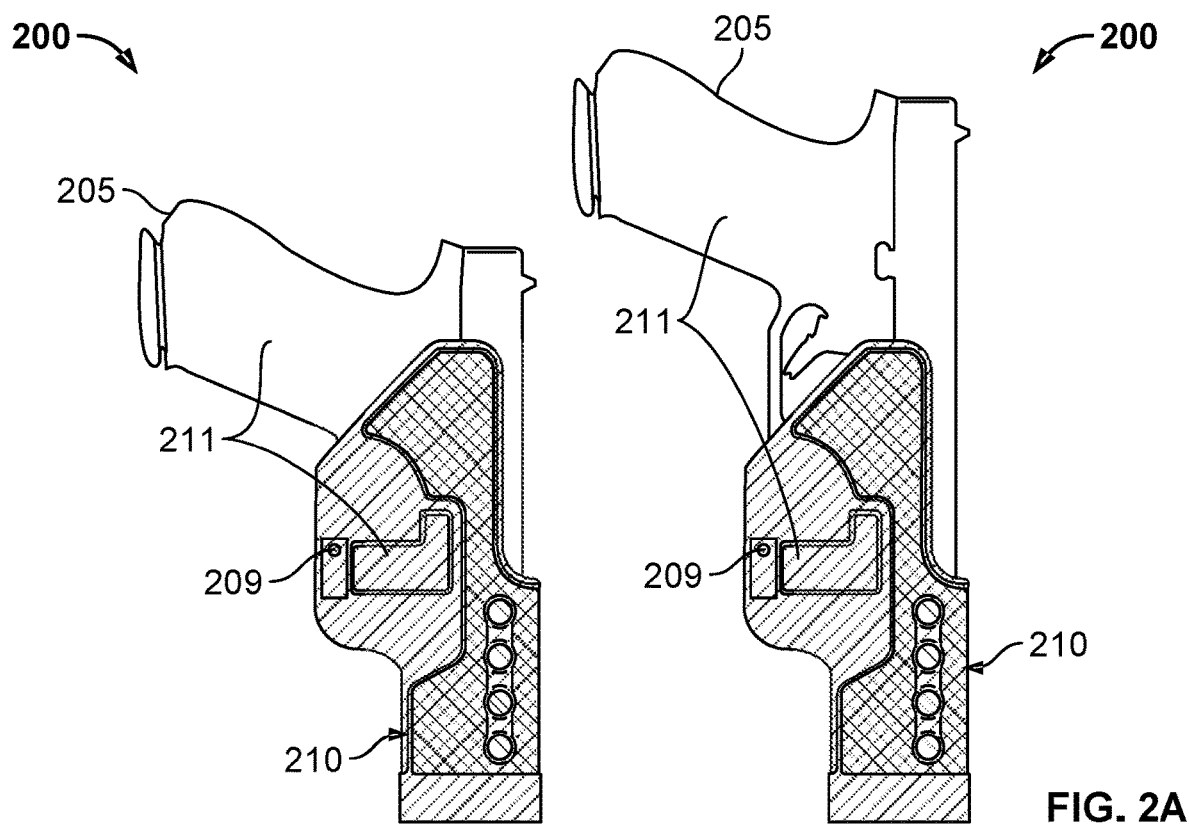
FIGS. 2A-2B are illustrations of example implementations of a weapon and a weapon holster that are part of a weapon alert safety protection system according to the present disclosure.
Figure 2B:
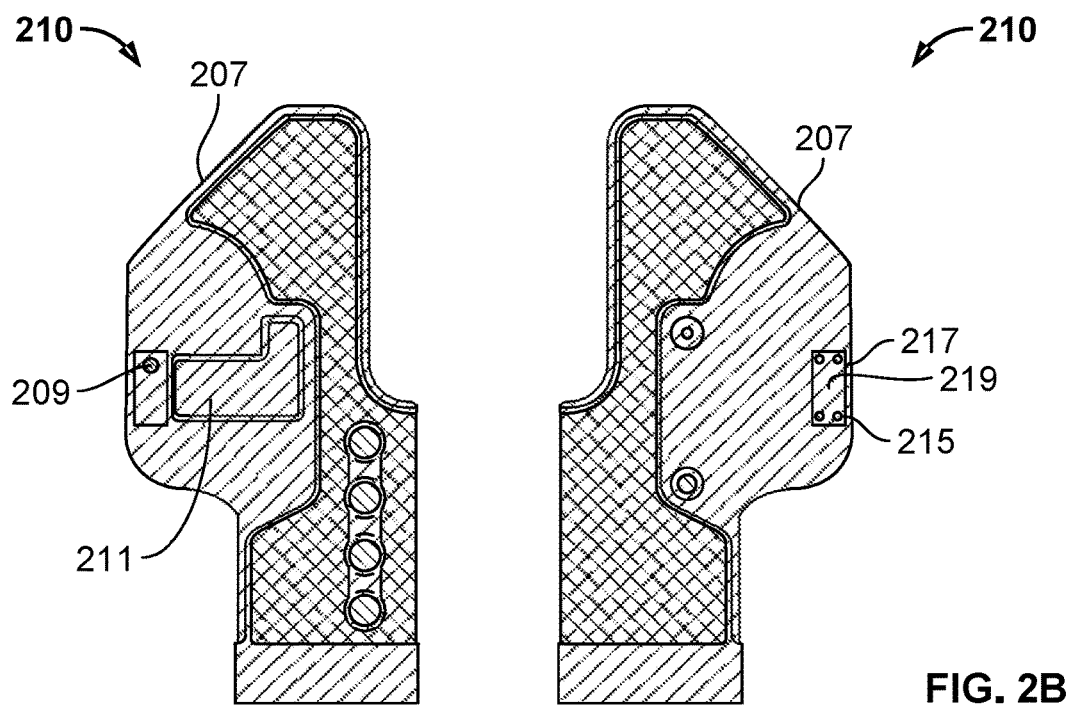

As described in more detail with respect to FIGS. 2A-2B, the weapon assembly 115 (and generally, any "weapon assembly" according to the present disclosure) includes a weapon and a weapon holder, such as a holster designed to hold and support at least a portion of the weapon for a user of the weapon, such as security personnel, law enforcement personnel, or other users. In the example implementation of the weapon assembly 115, the assembly 115 also includes a controller 111 (such as a micro-processor based controller), one or more GPS sensors 113, and one or more biometric feedback sensors 117. In some aspects, one or more of the controller 111, GPS sensors 113, and biometric feedback sensors 117 can be embedded in or integral with a weapon holster. In alternative aspects, one or more of the controller 111, GPS sensors 113, and biometric feedback sensors 117 can be embedded in or integral with a weapon. In other alternative aspects, one or more of the controller 111, GPS sensors 113, and biometric feedback sensors 117 can be embedded in or integral with the weapon and weapon holster in combination. Further, while not shown explicitly, the controller 111 includes an interface to communicate with the network 110.

In this example implementation, the network 110 comprises a digital data communication such as a communication network. Examples of communication networks include a local area network ("LAN"), a wide area network ("WAN"), peer-to-peer networks (having ad-hoc or static members), grid computing infrastructures, and the Internet.

The control system 105, generally, comprises a back-end server computing device (or devices) with one or more hardware processors and, for example, at least one database 103, a network interface 109, and one or more applications 107. At least one application 107 is a software application programmed to interface with the weapon assembly 115 through the network 110 to provide operations according to the processes and methods described in the present disclosure. Regardless of the particular implementation, "software" may include computer-readable instructions, firmware, wired or programmed hardware, or any combination thereof on a tangible medium (transitory or non-transitory, as appropriate) operable when executed to perform at least the processes and operations described herein. Indeed, each software component may be fully or partially written or described in any appropriate computer language including C, C++, Java, Visual Basic, ABAP, assembler, Perl, Python, .NET, Matlab, any suitable version of 4GL, as well as others. While portions of the software illustrated in FIG. 2 are shown as individual modules that implement the various features and functionality through various objects, methods, or other processes, the software may instead include a number of sub-modules, third party services, components, libraries, and such, as appropriate. Conversely, the features and functionality of various components can be combined into single components as appropriate.

The processor(s) (not shown) execute instructions and manipulates data to perform the operations of the application 107. The processor may be a central processing unit (CPU), a blade, an application specific integrated circuit (ASIC), a field-programmable gate array (FPGA), graphics processing unit (GPU), or another suitable component. Generally, the processor executes instructions and manipulates data to perform the operations of the application 107.

Although illustrated as a single database 103 in FIG. 1, two or more databases (or "memories") may be application 107. In some implementations, the database 103 is an in-memory database. In some aspects, database 103 is a cloud database (such as a Google database) that is located on one or more cloud based servers and secured for authentication by an administrator of the weapon alert safety protection system 100. The cloud database can be fully automated (without the need for human operator interaction) and is updated as the weapon alert safety protection system 100 performs the example processed described herein.

While database 103 is illustrated as an integral component of the control system 105, in some implementations, the database 103 can be external to the control system 107. The database 103 may include any memory or database module and may take the form of volatile or non-volatile memory including, without limitation, magnetic media, optical media, random access memory (RAM), read-only memory (ROM), removable media, or any other suitable local or remote memory component. The database 103 may store various objects or data, including classes, frameworks, applications, backup data, objects, jobs, web pages, web page templates, database tables, repositories storing business and/or dynamic information, and any other appropriate information including any parameters, variables, algorithms, instructions, rules, constraints, or references thereto associated with the purposes of the control system 105.

The illustrated control system 105, generally, is intended to encompass any computing device such as a desktop computer, laptop/notebook computer, wireless data port, smart phone, smart watch, wearable computing device, personal data assistant (PDA), tablet computing device, one or more processors within these devices, or any other suitable processing device. For example, the control system 105 may comprise a computer that includes an input device, such as a keypad, touch screen, or other device that can accept user information, and an output device that conveys information associated with the operation of the control system 105 itself, including digital data, visual information, or a GUI.

FIGS. 2A-2B are illustrations of example implementations of a weapon and a weapon holster that are part of the weapon alert safety protection system 100 of FIG. 1. As shown, a weapon assembly 200 (which can be used as the weapon assembly 115) includes a weapon 205 and a weapon holster 210. Although in this example implementation, the weapon 205 is a semi-automatic handgun, other weapons, such as revolvers, other pistols, and other firearms such as shotguns or rifles can be considered a weapon according to the present disclosure. As shown, the weapon holster 210 includes a pocket 207 to receive and secure at least a portion of the weapon 205 therein.

In this example implementation, the weapon holster 210 includes a controller 215 that is powered by a battery 217, each of which is mounted in or with the weapon holster 210. Generally, the controller 215 can include a processor-based micro-transceiver that allows the controller 215 to communicate (for example, with 3G, 4G, 5G, WiFi, or other protocol) to a back-end control system through a network (such as control system 105 through network 110 in FIG. 1). In this example implementation, the controller 215 includes, for example, a SIM7600E NODE MCU, that coordinates a workflow of the weapon assembly 200 during use of the weapon 205. In some aspects, the controller 215 is associated with a unique identification or reference alphanumeric string, for instance, to more specifically identify a user of the weapon 205.

A GPS sensor 219 can also be part of or communicably coupled to the controller 215 (and powered by the battery 217). In this example, the GPS sensor 219 can be or include a SIM28ML GPS sensor that generates a location (for example, longitude and latitude) of the weapon assembly 200 to provide to the controller 215. The controller 215 can, in some aspects, provide such detected location data to the back end control system.

The weapon assembly 200, as shown, includes one or more (and, in some aspects, multiple) biometric sensors 211, some of which can be mounted in the weapon 205 and some of which can be mounted in the weapon holster 210. The biometric sensors 211 can include, for example, one or more of a heart rate sensor, a galvanic skin response sensor, or a tension level sensor. The biometric sensors 211 can also include a sensor, such as a TCRT5000, that can detect a presence or absence of the weapon 205 in a secure position within the pocket 207 of the weapon holster 210. Each of the biometric sensors 211, therefore, is operable to measure certain characteristics of the user of the weapon 205, or the weapon 205 itself, and provide such measured characteristics to the controller 215.

The weapon assembly 200 also includes, in this implementation, an indicator light 209 that is embedded in or integral with the weapon holster 210. In some aspects, the indicator light 209 is communicably coupled to the controller 215 and can be adjusted (for example, turned on or off, turned from one color to another color) in response to instructions from the controller 215. In some aspects, adjustment of the indicator light 209 can be caused by instructions from the back-end control system that adjust the indicator light 209 to be indicative of a status of the weapon 205.

Figure 3A:
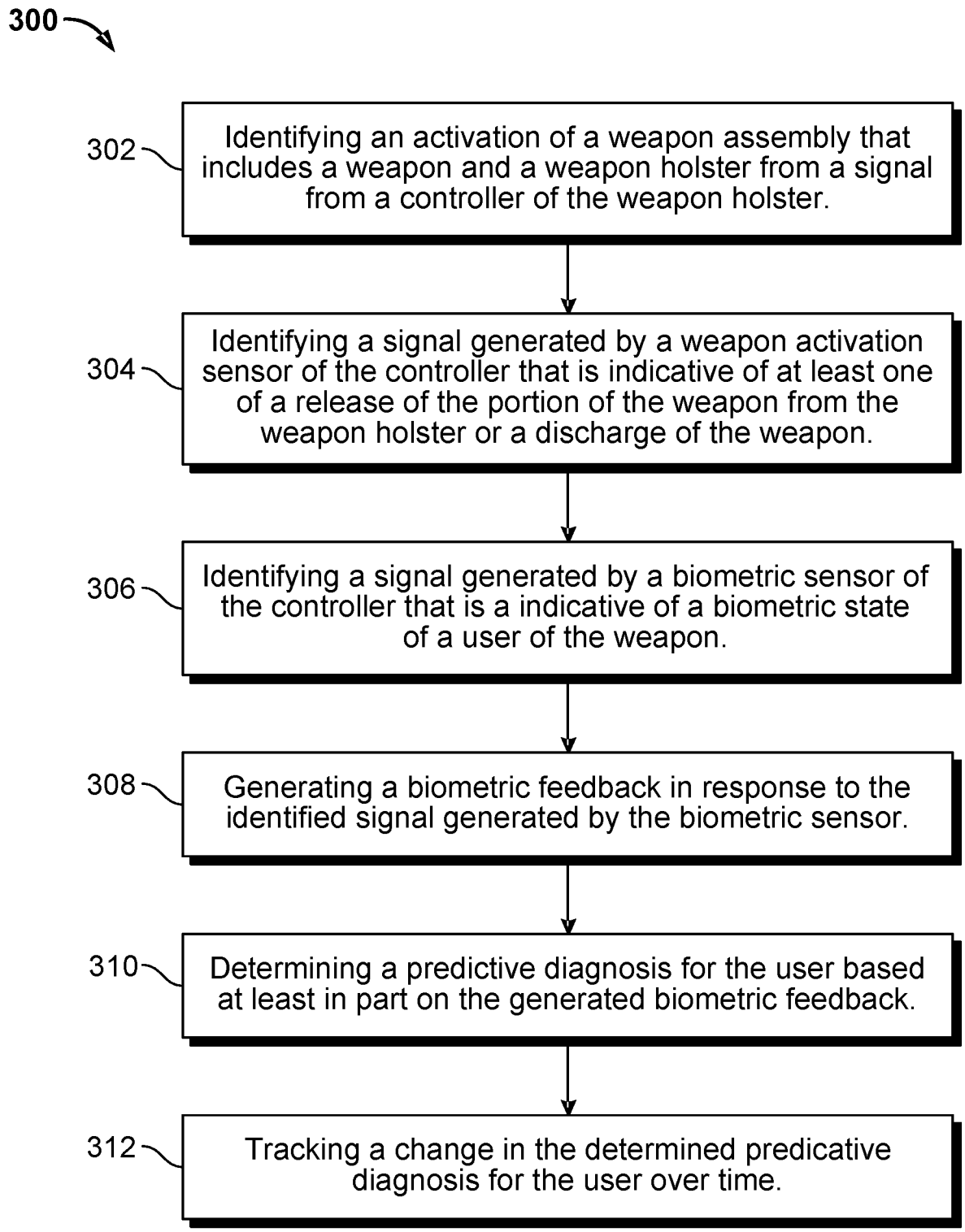
Figure 3C:
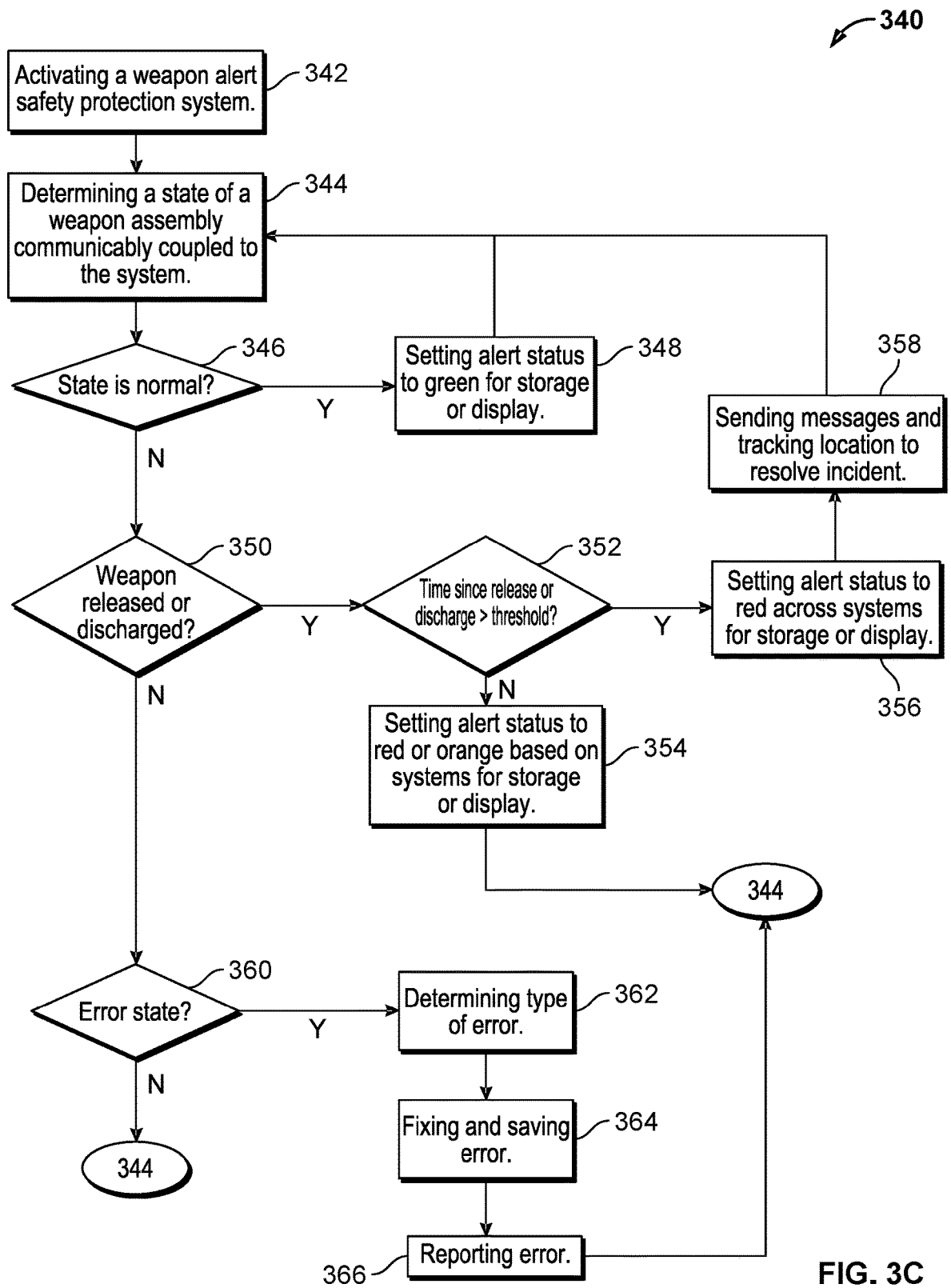

FIGS. 3A-3C are flowcharts that illustrate example methods performed with or by a weapon alert safety protection system according to the present disclosure. For example, methods of FIGS. 3A-3C can be performed with or by the weapon alert safety protection system 100 shown in FIG. 1.

FIG. 3A shows an example method 300 for managing a weapon, such as the weapon 115 (or weapon 200) as part of the weapon alert safety protection system 100 in FIG. 1. In some aspects, method 300 can include one or more steps taken by the control system 105 in the weapon alert safety protection system 100. Method 300 can begin at step 302, which includes identifying an activation of a weapon assembly that includes a weapon and a weapon holster from a signal from a controller of the weapon holster. For example, once the weapon assembly 115 (or weapon assembly 200) is activated (for example, automatically or by a user of the weapon assembly), a signal may be sent by the controller 111 to the control system 105 through the network 110. In some aspects, activation of the weapon assembly 115 can occur automatically when the controller 111 is activated (such as by checking to make sure the controller microtransceiver is installed and activated). In some aspects, once activated, the controller 111 can provide a GPS location and the unique identifier associated with the weapon assembly 115 to the control system 105.

Method 300 can continue at step 304, which includes identifying a signal generated by a weapon activation sensor of the controller that is indicative of at least one of a release of the portion of the weapon from the weapon holster or a discharge of the weapon. For example, in some aspects, a biometric feedback sensor 117 (or sensor 211) on the weapon holster or weapon can detect removal of the weapon from the holster. In some aspects, a biometric feedback sensor 117 (or sensor 211) or another sensor (for example, the TCRT5000) embedded in the weapon or weapon holster is operable to detect a discharge (firing) of the weapon. In any case, the sensor that detects the release or discharge (or both) provides a signal to the controller 111, which in turn sends the signal to the control system 105 through the network 110.

Method 300 can continue at step 306, which includes identifying a signal generated by a biometric sensor of the controller that is indicative of a biometric state of a user of the weapon. For example, one or more biometric feedback sensors 117 (or sensors 211) can detect certain biometric measurements, such as heart rate, tension, galvanic skin response, of the user of the weapon once the weapon has been released or discharged (or both). Such measurements (one or multiple) can be provided to the controller 111, and thereby provided to the control system 105 by the controller 111 through the network 110.

Method 300 can continue at step 308, which includes generating a biometric feedback in response to the identified signal generated by the biometric sensor. For example, the control system 105 can use the biometric measurements of the user to generate a biometric feedback. The feedback can include, for example, a determination of a state of the user based on the biometric measurements. For example, the biometric measurements can be indicative of a low stress state, for instance a state associated with a simple removal of the weapon for inspection or cleaning. As another example, the biometric measurements can be indicative of a medium stress state, for instance a state associated with a misfire of the weapon or discharge of the weapon not in a combat situation. As another example, the biometric measurements can be indicative of a high stress state, for instance a state associated with discharge of the weapon in a combat situation.

In some aspects, the stress state can be used to adjust a color or other state of the indicator light 209 on the weapon holster 210 (for example, as instructed by the control system 105 to the controller 111 or 215). For example, a low stress state can be indicated by a green light. A medium stress state can be indicated by an orange light. A high stress state can be indicated by a red light. Further, in some aspects, either of the stress states, such as medium or high, may activate GPS tracking of the weapon assembly 115.

Method 300 can continue at step 310, which includes determining a predictive diagnosis for the user based at least in part on the generated biometric feedback. For example, in cases where the biometric feedback is indicative of the low stress state, then the predictive diagnosis can be simply a check on the user of the weapon (such as a message or activation of indicator light to orange). But for a high stress state, the predictive diagnosis can include, for example, a post-traumatic stress diagnosis. In such cases, messages and GPS tracking can be provided by the control system 105. In addition, in some cases, the control system 105 can determine or help determine a corrective action based on the stress state. For example, corrective actions can include confirming the stress state, contacting the user of the weapon, providing immediate human assistance to the user of the weapon, or correcting an incident that caused the high stress state.

Method 300 can continue at step 312, which includes tracking a change in the determined predicative diagnosis for the user over time. For example, several predictive diagnosis can be made over time, for example, as method 300 repeats for a weapon user, iterations of the biometric measurements and biometric feedback can be accumulated by the control system 105 over time. Thus, independent predictive diagnoses can be generated by the control system 105 over time for the particular user. In some aspects, such independent predictive diagnoses that are generated can change over time, depending on the incidents that caused the release or discharge (or both) of the user's weapon.

FIG. 3B shows another example method 320 for managing a weapon, such as the weapon 115 (or weapon 200) as part of the weapon alert safety protection system 100 in FIG. 1. In some aspects, method 320 can include one or more steps taken by the controller 111 (or controller 215) in the weapon alert safety protection system 100. Method 320 can begin at step 322, which includes activating a weapon assembly that includes a weapon and a weapon holster that includes a controller. For example, the controller 111 (or controller 215) can be activated, for example, by the user of the weapon, a supervisor of the user of the weapon, or automatically by the controller 111 (or 215), itself. In some aspects, activation of the weapon assembly includes activation of one or more sensors that are part of the weapon assembly, such as biometric feedback sensors and GPS sensors. Upon activation, an indicator on the weapon assembly, such as the indicator light 209, can be set in a normal stage (such as a green color).

Method 320 can continue at step 324, which includes generating a signal by a weapon activation sensor of the controller that is indicative of at least one of a release of the portion of the weapon from the weapon holster or a discharge of the weapon. For example, in some aspects, the biometric feedback sensor 117 (or sensor 211) on the weapon holster or weapon can detect removal of the weapon from the holster. In some aspects, a biometric feedback sensor 117 (or sensor 211) or another sensor (for example, the TCRT5000) embedded in the weapon or weapon holster is operable to detect a discharge (firing) of the weapon. In any case, the sensor that detects the release or discharge (or both) provides a signal to the controller 111 of the weapon assembly.

Method 320 can continue at step 326, which includes generating a signal by a biometric sensor of the controller that is indicative of a biometric state of a user of the weapon. For example, one or more biometric feedback sensors 117 (or sensors 211) can detect certain biometric measurements, such as heart rate, tension, galvanic skin response, of the user of the weapon once the weapon has been released or discharged (or both). Such measurements (one or multiple) can be provided to the controller 111. As previously described, the control system 105 can use the biometric measurements of the user to generate a biometric feedback. The feedback can include, for example, a determination of the state of the user based on the biometric measurements, such as the low state, medium state, or high state.

Method 320 can continue at step 328, which includes generating a signal by a GPS sensor of the controller that is indicative of a location of the user of the weapon. For example, in some aspects, the GPS sensor 113 can continuously provide location data to the controller 111 subsequent to activation of the weapon assembly (in step 322). In other aspects, the GPS sensor 113 can continuously provide location data to the controller 111 only when the state of the user is determined to be the medium or high state. In other aspects, the GPS sensor 113 can continuously provide location data to the controller 111 only when the state of the user is determined to be the high state Method 320 can continue at step 330, which includes receiving an alert associated with at least one of a biometric feedback in response to the generated signal by the biometric sensor or the location of the user. For example, based on the state of the user determined by the control system 105, or the location provided by the weapon assembly 115, one or more alerts or messages can be provided from the control system 105 to the weapon assembly 115 (such as through the indicator light 209) or to the user. The alert can include, for example, text messages, phone calls from a human operator at the control system 105 (or command center), or other type of alert.

FIG. 3C shows another example method 340 for managing a weapon, such as the weapon 115 (or weapon 200) as part of the weapon alert safety protection system 100 in FIG. 1. In some aspects, method 340 can include one or more steps taken by the control system 105 in combination with the controller 111 (or controller 215) in the weapon alert safety protection system 100. Method 340 can begin at step 342, which includes activating a weapon alert safety protection system. For example, a controller of the weapon assembly can be activated, for example, by the user of the weapon, a supervisor of the user of the weapon, automatically by the controller, or by a control system communicably coupled to the controller of the weapon assembly. In some aspects, activation of the weapon assembly includes activation of one or more sensors that are part of the weapon assembly, such as biometric feedback sensors and GPS sensors.

Figure 4A:
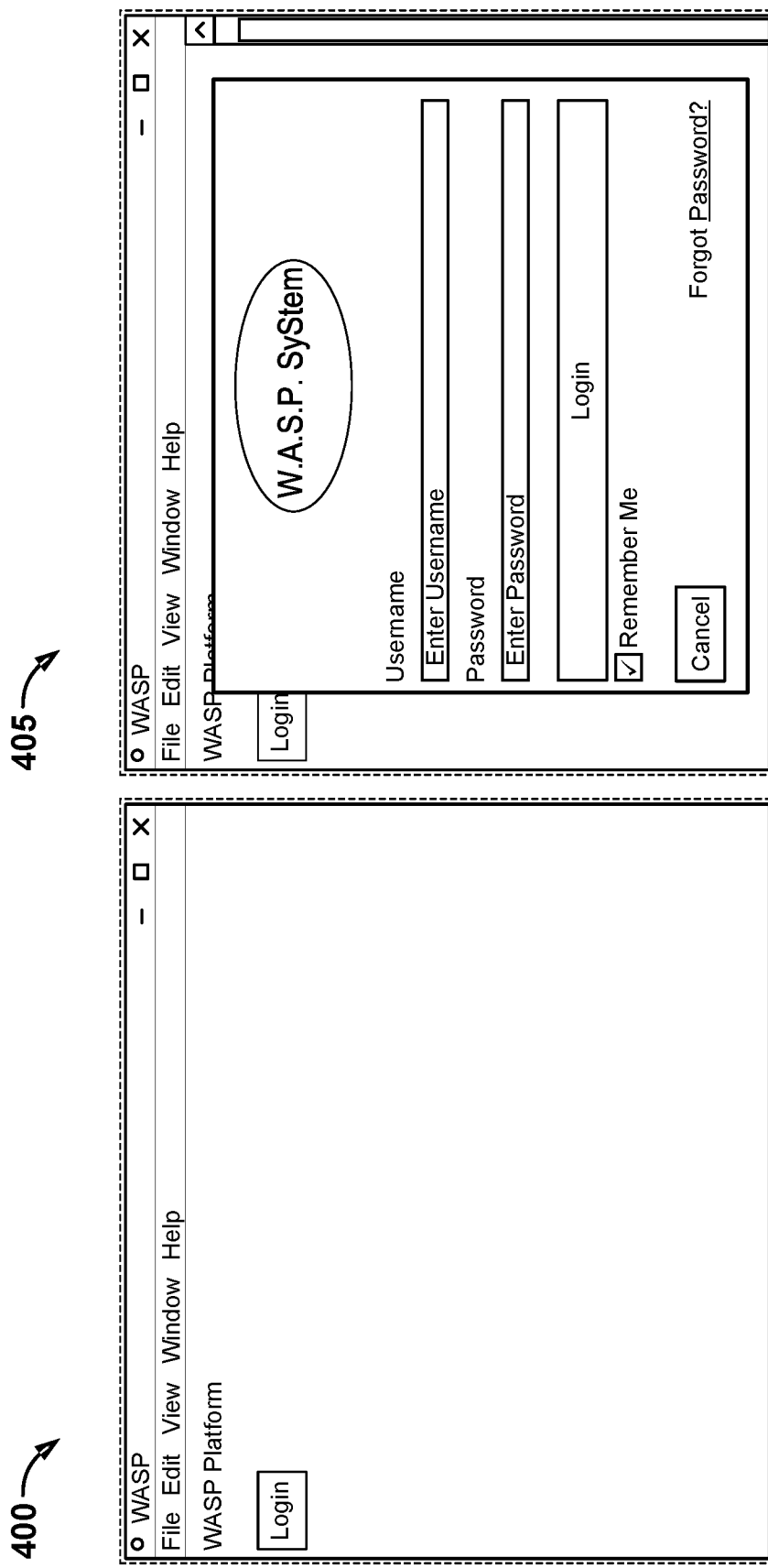

In some aspects, step 342 also includes activation of the control system that is communicably coupled to the weapon assembly. In some aspects, activation of the control system includes a human operator, such as at a command center in which the control system is located, logging into an application (for example, application 107) on the control system (control system 105). Turning briefly to FIG. 4A, this figure illustrates a graphical user interface 400 that provides an example of an initial login screen for the control system 105 of the weapon alert safety protection system 100. Graphical user interface 405 provides an example of a login screen for the control system 105 of the weapon alert safety protection system 100 in FIG. 4A, where a user can enter credentials to activate the application 107.

Figure 4B:
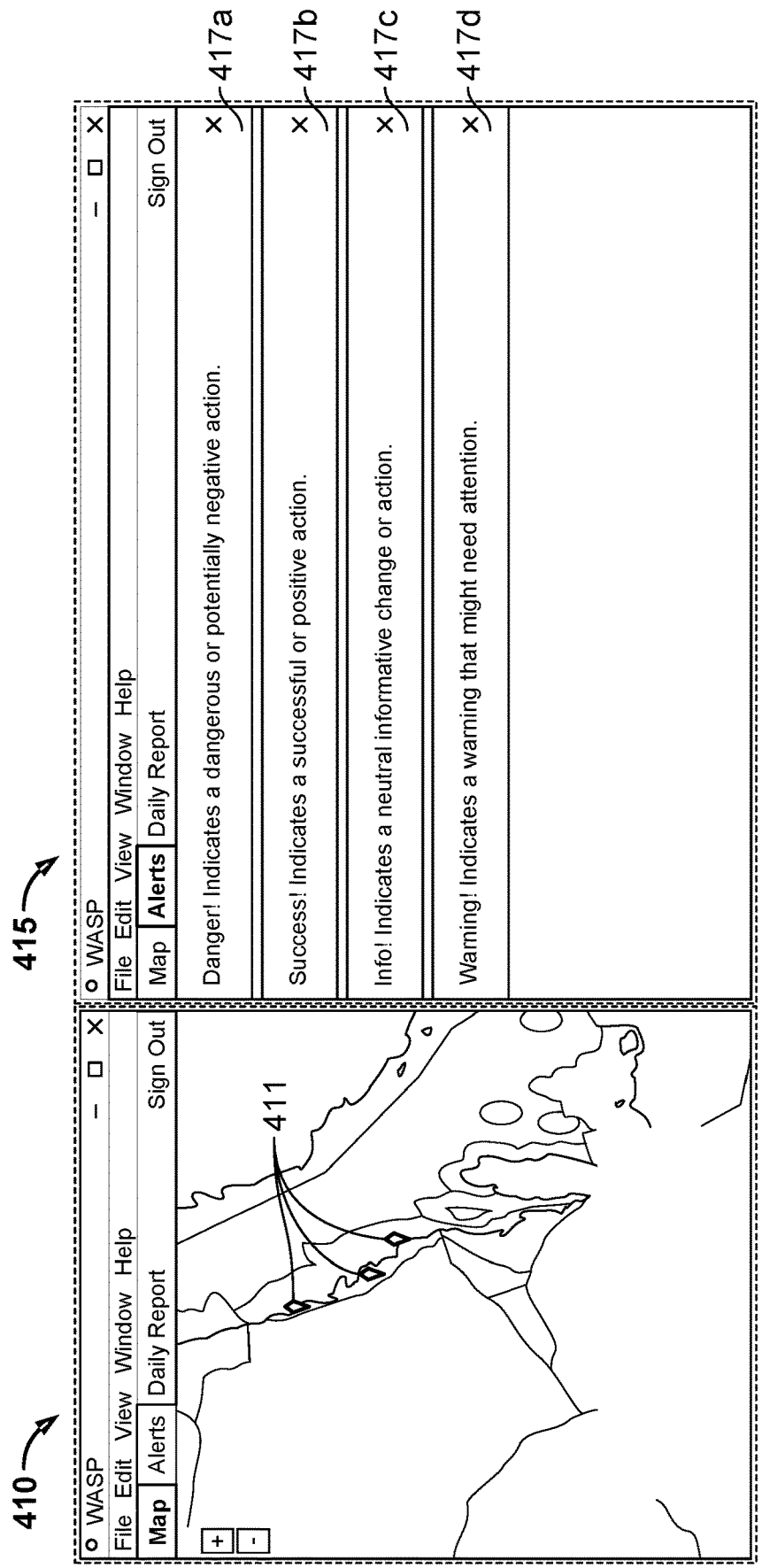

In some aspects, step 342 also includes activation of a GPS sensor of the controller and communication of the location of the weapon assembly to the control system. Turning briefly to FIG. 4B, this figure illustrates a graphical user interface 410 that provides a map showing different locations 411 of weapons assemblies across the map area.

Method 340 can continue at step 344, which includes determining a state of a weapon assembly communicably coupled to the system. For example, the weapon assembly can be in one of several states, including a normal state in which the weapon is holstered in the weapon holster and the controller is operating normally (a green state). Another state can include a warning state, in which the weapon is released from the holster but for a short period of time, such as below a threshold time duration (for example, 30 seconds). This states can be an orange state. Another state can include an emergency state, in which the weapon is released from the holster for longer than the threshold time duration (for example, 30 seconds) or when the weapon has been discharged. This states can be a red state. Other states can include a low data state (a blue state) or an error state (a yellow state). Turning briefly to FIG. 4B, this figure illustrates a graphical user interface 415 that provides an example of the possible states of the weapons assemblies, including the emergency state 417a, the normal state 417b, the low data state 417c, and the warning state 417d.

Method 340 can continue at step 346, which includes determining whether the state of a weapon assembly is at the normal state. If the determination is yes, then method 340 can continue at step 348, which includes setting an alert status to green for storage or display. For example, the indicator light 209 may be set to green on the weapon holster 210, while the control system sets the state for the particular weapons assembly at green also. Method 340 can then return to step 344.

If the determination is no, then method 340 can continue at step 350, which includes a determination of whether the weapon is released (for instance, from the weapon holster) or discharged (in other words, fired). If the determination is yes, then method 340 can continue at step 352, which includes a determination of whether a time since the release or discharge is greater than a threshold time. If the determination is yes, then method 340 can continue at step 356, which includes setting the alert status to red across systems for storage or display. For example, if the weapon has been released from the holster for a period of time longer than the threshold time (for example, longer than 30 seconds), it may be considered that an incident that caused the extended release of the weapon from the holster is an emergency, such as a combat or weapon discharge situation. Thus, after the determination in 352, then the status at the weapon (for example, the indicator light) and the control system can be changed to red (an emergency state).

Method 340 can the continue at step 358, which includes sending messages and tracking a location of the weapon to resolve the incident. For example, in the emergency state, the weapon assembly can be tracked (by GPS location) and alerts or messages can be provided to the user of the weapon. In some aspects, step 358 also includes tracking of biometric measurements performed by sensors that are included with or coupled to the controller of the weapon (for example, to provide a biometric feedback and/or predictive diagnosis over time). Method 340 can then return to step 344.

If the determination in step 352 is no, then method 340 can continue to step 354, which includes setting the alert status to red or orange based on systems for storage or display. For example, if the weapon has been released from the holster for a period of time less than the threshold time (for example, less than 30 seconds), it may be considered that an incident that caused the extended release of the weapon from the holster is not an emergency and can be, for example, an inspection of the weapon by the user. In such a case, the indicator light on the weapon (for example, indicator light 209) can be set to red, while the status of the weapon at the control system 105 can be set to orange (a warning state). Method 340 can then return to step 344.

If the determination in step 350 is no, then method 340 can continue at step 360, which includes a determination of whether the weapon assembly is in an error state. Example error states include an error in connection between the control system and controller, a dysfunctional system (a hardware or software problem), and an inoperable battery on the weapon assembly, among others. If the determination is yes, the method 340 can continue at step 362, which includes determining a type of the error. Method 340 can then continue at step 364, which includes fixing and saving the error. For example, errors can be saved in the database of the control system in order to catalog a device error history and associated fixes in order to optimize the fix time if certain errors occur repeatedly (with the same weapon or other weapons). Method 340 can then continue at step 366, which includes reporting the error. For example, turning briefly to FIG. 4C, this figure shows graphical user interface 420. As an example, the interface 420 illustrates an example of a Daily Report available to an operator at a command center that provides daily information about errors of weapon assemblies, as well as other information. Method 340 can then return to step 344. If the determination in step 360 is no, the method 340 can continue return to step 344.

Figure 5:
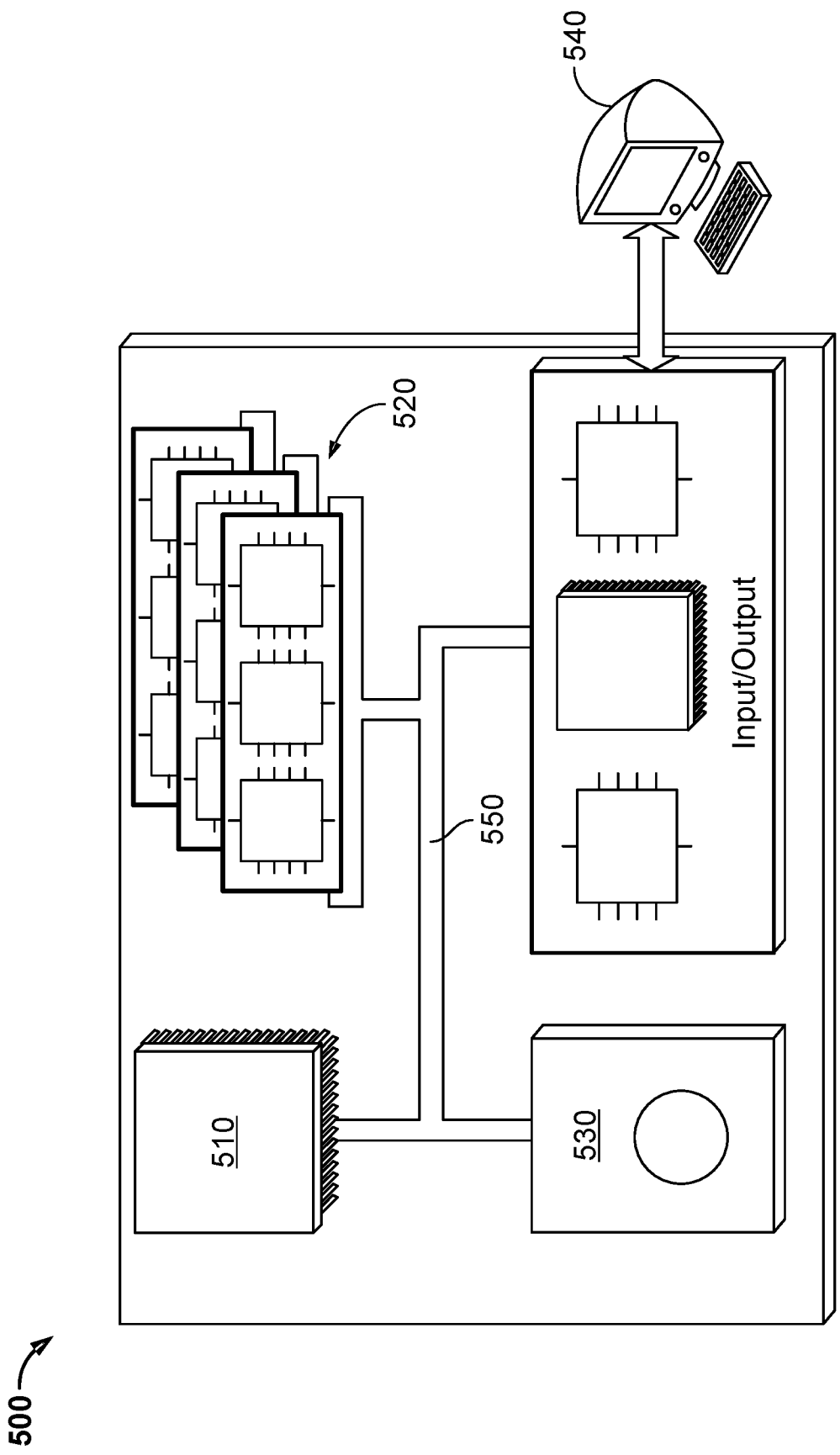
FIG. 5 is a schematic illustration of an example control system of a weapon alert safety protection system according to the present disclosure.

FIG. 5 is a schematic illustration of an example controller 500 (or control system) for managing a weapon assembly, such as the weapon assembly 115. For example, all or parts of the controller 500 can be used for the operations described previously, for example as or as part of the control system 105. The controller 500 is intended to include various forms of digital computers, such as printed circuit boards (PCB), processors, digital circuitry, or otherwise. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 500 includes a processor 510, a memory 520, a storage device 530, and an input/output device 540. Each of the components 510, 520, 530, and 540 are interconnected using a system bus 550. The processor 510 is capable of processing instructions for execution within the controller 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the controller 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the controller 500. In one implementation, the storage device 530 is a computer-readable medium. In various different implementations, the storage device 530 may be a floppy disk device, a hard disk device, an optical disk device, a tape device, flash memory, a solid state device (SSD), or a combination thereof The input/output device 540 provides input/output operations for the controller 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, solid state drives (SSDs), and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) or LED (light-emitting diode) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A weapon assembly, comprising:
   a weapon;
   a weapon holster configured to receive and support at least a portion of the weapon; and
   a controller that includes at least one biometric sensor, at least one weapon activation sensor, and at least one interface configured to communicably couple to a control system, at least one of the controller or the control system configured to perform operations comprising:
      transmitting, from the controller to the control system, a signal generated by the at least one weapon activation sensor that is indicative of at least one of a release of the portion of the weapon from the weapon holster or a discharge of the weapon;
      transmitting, from the controller to the control system, a signal generated by the at least one biometric sensor indicative of a biometric state of a user of the weapon subsequent to the at least one of the release of the portion of the weapon from the weapon holster or the discharge of the weapon, wherein the signal generated by the at least one biometric sensor is processable by the control system to generate a biometric feedback to determine a predictive diagnosis for the user of the weapon,
      determining that the signal generated by the at least one weapon activation sensor is indicative of the discharge of the weapon, and
      determining a type of the discharge of the weapon, wherein determining the type of the discharge of the weapon comprises: determining a time duration subsequent to the release of the portion of the weapon from the weapon holster, comparing the determined time duration against a pre-determined threshold time duration; and determining the type of the discharge of the weapon based on the comparison.

2. The weapon assembly of claim 1, further comprising a GPS sensor, the controller configured to perform operation further comprising:
   transmitting, to the control system, a location of the user or the weapon holster based on one or more signals from the GPS sensor, subsequent to transmitting the signal generated by the at least one weapon activation sensor that is indicative of the at least one of the release of the portion of the weapon from the weapon holster or the discharge of the weapon; and
   receiving, from the control system, an alert associated with at least one of the generated biometric feedback or the location of the user of weapon holster.

3. The weapon assembly of claim 1, wherein the identified signal generated by the at least one biometric sensor is processable by the control system to determine a level of biometric stress of the user based on the identified signal generated by the at least one biometric sensor.

4. The weapon assembly of claim 3, wherein the level of biometric stress comprises one of a low stress level, a medium stress level, or a high stress level.

5. The weapon assembly of claim 4, wherein the at least one biometric sensor comprises at least one of a heart rate sensor, a galvanic skin response sensor, or a tension level sensor.

6. The weapon assembly of claim 1, wherein the weapon comprises a handgun.

7. A weapon management system, comprising:
   a weapon assembly that comprises a weapon and a weapon holster, the weapon holster configured to receive and support at least a portion of the weapon and comprising a controller that includes at least one biometric sensor and at least one weapon activation sensor; and a control system that comprises at least one interface configured to communicably couple to the controller and perform operations comprising:
  identifying a signal generated by the at least one weapon activation sensor that is indicative of at least one of a release of the portion of the weapon from the weapon holster or a discharge of the weapon;
  identifying a signal generated by the at least one biometric sensor indicative of a biometric state of a user of the weapon subsequent to the at least one of the release of the portion of the weapon from the weapon holster or the discharge of the weapon;
  generating a biometric feedback in response to the identified signal generated by the at least one biometric sensor;
  determining a predictive diagnosis for the user based at least in part on the generated biometric feedback;
  determining that the signal generated by the at least one weapon activation sensor is indicative of the discharge of the weapon; and
  determining a type of the discharge of the weapon, wherein the operation of determining the type of the discharge of the weapon comprises:
    determining a time duration subsequent to the release of the portion of the weapon from the weapon holster;
    comparing the determined time duration against a pre-determined threshold time duration; and
    determining the type of the discharge of the weapon based on the comparison.

8. The system of claim 7, wherein the controller further comprises a GPS sensor, and the control system is configured to perform operation further comprising:
  tracking a location of at the weapon holster, based on one or more signals from the GPS sensor, subsequent to identifying the signal generated by the at least one weapon activation sensor that is indicative of the at least one of the release of the portion of the weapon from the weapon holster or the discharge of the weapon.

9. The system of claim 7, wherein the type of discharge of the weapon comprises a misfire or a combat shot.

10. The system of claim 7, wherein the operation of generating the biometric feedback in response to the identified signal generated by the at least one biometric sensor comprises:
  determining a level of biometric stress of the user based on the identified signal generated by the at least one biometric sensor; and
  storing the level of biometric stress in at least one database of the control system.

11. The system of claim 10, wherein the level of biometric stress comprises one of a low stress level, a medium stress level, or a high stress level.

12. The system of claim 10, wherein the operation of determining the level of biometric stress of the user based on the identified signal generated by the at least one biometric sensor comprises measuring at least one of a heart rate of the user, a galvanic skin response of the user, or a tension level of the user by the at least one biometric sensor.

13. The system of claim 7, wherein the control system is configured to perform operations further comprising:
  storing the determined predictive diagnosis for the user; and
  tracking a change in the determined predicative diagnosis for the user over time.

14. The system of claim 7, wherein the control system is configured to perform operations further comprising:
  generating an alert based at least in part on the generated biometric feedback; and
  transmitting the generated alert to a command center associated with the user.

15. The system of claim 7, wherein the weapon comprises a handgun.

16. A computer-implemented method for managing a weapon, comprising:
  identifying, with one or more hardware processors, an activation of a weapon assembly that comprises a weapon and a weapon holster, the activation based on a signal from a controller of the weapon holster that includes at least one biometric sensor and at least one weapon activation sensor;
  identifying, with the one or more hardware processors, a signal generated by the at least one weapon activation sensor that is indicative of at least one of a release of the portion of the weapon from the weapon holster or a discharge of the weapon;
  identifying, with the one or more hardware processors, a signal generated by the at least one biometric sensor indicative of a biometric state of a user of the weapon subsequent to the at least one of the release of the portion of the weapon from the weapon holster or the discharge of the weapon;
  generating, with the one or more hardware processors, a biometric feedback in response to the identified signal generated by the at least one biometric sensor;
  determining, with the one or more hardware processors, a predictive diagnosis for the user based at least in part on the generated biometric feedback;
  determining, with the one or more hardware processors, that the signal generated by the at least one weapon activation sensor is indicative of the discharge of the weapon; and
  determining, with the one or more hardware processors, a type of the discharge of the weapon, wherein determining the type of the discharge of the weapon comprises:
    determining, with the one or more hardware processors, a time duration subsequent to the release of the portion of the weapon from the weapon holster;
    comparing, with the one or more hardware processors, the determined time duration against a pre-determined threshold time duration; and
    determining, with the one or more hardware processors, the type of the discharge of the weapon based on the comparison.

17. The computer-implemented method of claim 16, wherein the controller further comprises a GPS sensor, and the method further comprises:
  tracking, with the one or more hardware processors, a location of at the weapon holster, based on one or more signals from the GPS sensor, subsequent to identifying the signal generated by the at least one weapon activation sensor that is indicative of the at least one of the release of the portion of the weapon from the weapon holster or the discharge of the weapon.

18. The computer-implemented method of claim 16, wherein the type of discharge of the weapon comprises a misfire or a combat shot.

19. The computer-implemented method of claim 16, wherein generating the biometric feedback in response to the identified signal generated by the at least one biometric sensor comprises:

determining, with the one or more hardware processors, a level of biometric stress of the user based on the identified signal generated by the at least one biometric sensor; and storing, with the one or more hardware processors, the level of biometric stress in at least one database of the control system.

20. The computer-implemented method of claim 19, wherein the level of biometric stress comprises one of a low stress level, a medium stress level, or a high stress level.

21. The computer-implemented method of claim 19, wherein determining the level of biometric stress of the user based on the identified signal generated by the at least one biometric sensor comprises identifying, with the one or more hardware processors, one or more measurements of at least one of a heart rate of the user, a galvanic skin response of the user, or a tension level of the user by the at least one biometric sensor.

22. The computer-implemented method of claim 16, further comprising:
storing, with the one or more hardware processors, the determined predictive diagnosis for the user; and
tracking, with the one or more hardware processors, a change in the determined predicative diagnosis for the user over time.

23. The computer-implemented method of claim 16, further comprising:
generating, with the one or more hardware processors, an alert based at least in part on the generated biometric feedback; and
transmitting, with the one or more hardware processors, the generated alert to a command center associated with the user.

24. The computer-implemented method of claim 16, wherein the weapon comprises a handgun.

25. An apparatus comprising a tangible, non-transitory computer readable media that includes instructions that, when executed by one or more hardware processors, cause the one or more hardware processors to perform operations comprising:
identifying an activation of a weapon assembly that comprises a weapon and a weapon holster, the activation based on a signal from a controller of the weapon holster that includes at least one biometric sensor and at least one weapon activation sensor;
identifying a signal generated by the at least one weapon activation sensor that is indicative of at least one of a release of the portion of the weapon from the weapon holster or a discharge of the weapon;
identifying a signal generated by the at least one biometric sensor indicative of a biometric state of a user of the weapon subsequent to the at least one of the release of the portion of the weapon from the weapon holster or the discharge of the weapon;
generating a biometric feedback in response to the identified signal generated by the at least one biometric sensor;
determining a predictive diagnosis for the user based at least in part on the generated biometric feedback;
determining that the signal generated by the at least one weapon activation sensor is indicative of the discharge of the weapon; and
determining a type of the discharge of the weapon, wherein the operation of determining the type of the discharge of the weapon comprises:
determining a time duration subsequent to the release of the portion of the weapon from the weapon holster;
comparing the determined time duration against a predetermined threshold time duration; and
determining the type of the discharge of the weapon based on the comparison.

26. The apparatus of claim 25, wherein the controller further comprises a GPS sensor, and the operations further comprise:
tracking a location of at the weapon holster, based on one or more signals from the GPS sensor, subsequent to identifying the signal generated by the at least one weapon activation sensor that is indicative of the at least one of the release of the portion of the weapon from the weapon holster or the discharge of the weapon.

27. The apparatus of claim 25, wherein the type of discharge of the weapon comprises a misfire or a combat shot.

28. The apparatus of claim 25, wherein the operation of generating the biometric feedback in response to the identified signal generated by the at least one biometric sensor comprises:
determining a level of biometric stress of the user based on the identified signal generated by the at least one biometric sensor; and
storing the level of biometric stress in at least one database of the control system.

29. The apparatus of claim 28, wherein the level of biometric stress comprises one of a low stress level, a medium stress level, or a high stress level.

30. The apparatus of claim 28, wherein the operation of determining the level of biometric stress of the user based on the identified signal generated by the at least one biometric sensor comprises identifying one or more measurements of at least one of a heart rate of the user, a galvanic skin response of the user, or a tension level of the user by the at least one biometric sensor.

31. The apparatus of claim 25, wherein the operations further comprise:
storing the determined predictive diagnosis for the user; and
tracking a change in the determined predicative diagnosis for the user over time.

32. The apparatus of claim 25, wherein the operations further comprise:
generating an alert based at least in part on the generated biometric feedback; and
transmitting the generated alert to a command center associated with the user.

33. The apparatus of claim 25, wherein the weapon comprises a handgun.

* * * * *